United States Patent
Shah et al.

(10) Patent No.: US 12,018,225 B2
(45) Date of Patent: Jun. 25, 2024

(54) SUCCINIMIDE DISPERSANTS POST-TREATED WITH HETEROAROMATIC GLYCIDYL ETHERS THAT EXHIBIT GOOD SOOT HANDLING PERFORMANCE

(71) Applicant: CHEVRON ORONITE COMPANY LLC, San Ramon, CA (US)

(72) Inventors: Priyank N. Shah, Fremont, CA (US); Morgan L. Miller, Fairfield, CA (US)

(73) Assignee: CHEVRON ORONITE COMPANY LLC, San Ramon, CA (US)

( * ) Notice: Subject to any disclaimer, the term of this patent is extended or adjusted under 35 U.S.C. 154(b) by 0 days.

(21) Appl. No.: 18/016,499

(22) PCT Filed: Jul. 22, 2021

(86) PCT No.: PCT/IB2021/056637
§ 371 (c)(1),
(2) Date: Jan. 17, 2023

(87) PCT Pub. No.: WO2022/018682
PCT Pub. Date: Jan. 27, 2022

(65) Prior Publication Data
US 2023/0323236 A1    Oct. 12, 2023

Related U.S. Application Data

(60) Provisional application No. 63/055,547, filed on Jul. 23, 2020.

(51) Int. Cl.
| | | |
|---|---|---|
| *C10M 177/00* | (2006.01) | |
| *C07D 303/22* | (2006.01) | |
| *C10M 133/56* | (2006.01) | |
| *C10N 30/04* | (2006.01) | |
| *C10N 40/25* | (2006.01) | |
| *C10N 60/06* | (2006.01) | |

(52) U.S. Cl.
CPC ......... *C10M 177/00* (2013.01); *C07D 303/22* (2013.01); *C10M 133/56* (2013.01); C10M 2203/003 (2013.01); C10M 2215/28 (2013.01); C10M 2215/30 (2013.01); *C10N 2030/041* (2020.05); *C10N 2040/25* (2013.01); *C10N 2060/06* (2013.01)

(58) Field of Classification Search
CPC ..... C07D 3/22; C10M 133/56; C10M 177/00; C10M 2203/003; C10M 2203/1025; C10M 2215/28; C10M 2215/30; C10N 2030/041; C10N 2040/25; C10N 2060/06
See application file for complete search history.

(56) References Cited

U.S. PATENT DOCUMENTS 4,617,137 A * 10/1986 Plavac ................... C10L 1/224
548/545
2019/0390130 A1    12/2019 Chommeloux

FOREIGN PATENT DOCUMENTS

EP        2379686        10/2011

OTHER PUBLICATIONS

International Search Report, issued on Oct. 22, 2021, during the prosecution of International Application No. PCT/IB2021/056637.
Written Opinion of the International Searching Authority, issued on Oct. 22, 2021, during the prosecution of International Application No. PCT/IB2021/056637.

* cited by examiner

*Primary Examiner* — James C Goloboy

(57) ABSTRACT

A dispersant composition is described. The composition includes a succinimide dispersant composition comprising a reaction product of a hydrocarbyl succinimide and a heteroaromatic glycidyl ether having a structure:

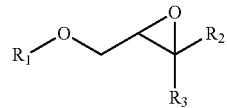

wherein $R_1$ is a heteroaryl or heteroarylalkyl group having 4 to 20 carbon atoms, and $R_2$ and $R_3$ are independently a hydrogen atom, an alkyl group, or an aryl group.

26 Claims, No Drawings

SUCCINIMIDE DISPERSANTS POST-TREATED WITH HETEROAROMATIC GLYCIDYL ETHERS THAT EXHIBIT GOOD SOOT HANDLING PERFORMANCE

TECHNICAL FIELD

This disclosure relates to lubricating oil additive compositions. More specifically, this disclosure describes dispersant additive compositions, lubricating oil compositions containing the same and methods for using the compositions thereof.

BACKGROUND

Dispersants can be added to lubricating oils to keep vital engine parts clean, prolong life, maintain proper emissions, and achieve good fuel economy.

Perhaps the most widely used dispersants are succinimides. A succinimide dispersant typically has a polar head and a long hydrocarbon tail. The polar head can attach to the insoluble material such as soot, sludge, and other impurities while the long hydrocarbon tail keeps the dispersant suspended in oil. Once several dispersant polar heads have attached themselves to a solid particle, it can no longer combine with other impurities to form large particles that can deposit onto engine surfaces but is rather removed from the engine when the oil is changed.

Conversely, failure to have adequate dispersancy can result in sludge flocculation, precipitation of the insoluble materials, soot particle agglomeration, deposit formation, filter plugging, oil thickening, wear, and the like.

There are many ongoing efforts in the lubricant industry aimed to improve dispersancy.

SUMMARY

In one aspect, there is provided a dispersant composition comprising: a succinimide dispersant composition comprising a reaction product of a hydrocarbyl succinimide and a heteroaromatic glycidyl ether having a structure:

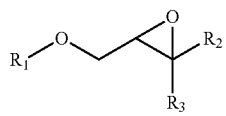

wherein $R_1$ is a heteroaryl or heteroarylalkyl group having 4 to 20 carbon atoms, and $R_2$ and $R_3$ are independently a hydrogen atom, an alkyl group, or an aryl group.

In another aspect, there is provided a lubricating oil composition comprising: a base oil; a succinimide dispersant composition comprising a reaction product of a hydrocarbyl succinimide and a heteroaromatic glycidyl ether having a structure:

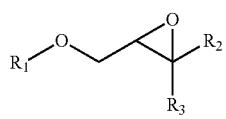

wherein $R_1$ is a heteroaryl or heteroarylalkyl having 4 to 20 carbon atoms, and $R_2$ and $R_3$ are independently a hydrogen atom, an alkyl group, or an aryl group.

In another aspect, there is provided a method of reducing soot-induced viscosity increase in an engine, the method comprising: introducing a dispersant composition to the engine, wherein the dispersant composition comprises: a succinimide dispersant comprising a reaction product of a polyalkenyl succinimide and a heteroaromatic glycidyl ether having a structure:

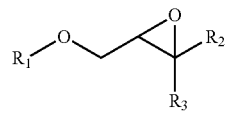

wherein $R_1$ is a heteroaryl or heteroarylalkyl group having 4 to 20 carbon atoms, and $R_2$ and $R_3$ are independently a hydrogen atom, an alkyl group, or an aryl group; and operating the engine.

DETAILED DESCRIPTION

Definitions

The following terms used with the description are defined as such:

The term "succinimide" is understood in the art to include many of the amide, imide, and amidine species which may be formed by the reaction of a succinic anhydride with an amine. The predominant product, however, is a succinimide and this term has been generally accepted as meaning the product of a reaction of an alkenyl- or alkyl-substituted succinic acid or anhydride with an amine. Alkenyl or alkyl succinimides are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746.

The term "post-treating agent" refers to reagents capable of functionalizing succinimides.

The term "hydrocarbyl" refers to a chemical group or moiety derived from hydrocarbons including saturated and unsaturated hydrocarbons. Examples of hydrocarbyl groups include alkenyl, alkyl, polyalkenyl, polyalkyl, phenyl, and the like.

The term "PIBSA" is an abbreviation for polyisobutenyl or polyisobutyl succinic anhydride.

The terms 'oil-soluble' or 'oil-dispersible' as used herein do not necessarily indicate that the compounds or additives are soluble, dissolvable, miscible or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

The present invention describes novel dispersant additive compositions and lubricating oil compositions containing the same. According to one or more embodiments, the present invention provides a dispersant formulation comprising a first dispersant (or primary dispersant) and optionally, a second dispersant (or secondary dispersant). The first dispersant (or primary dispersant) is a succinimide that has been post-treated by a heteroaromatic glycidyl ether shown in Structure I below. The second dispersant (or secondary dispersant) is a succinimide with or without post-treatment. In some embodiments, the dispersant formulation includes a third dispersant, wherein the third dispersant is a Mannich dispersant.

The present invention also describes a method of reducing soot-induced viscosity increase in an engine, wherein a dispersant formulation or a lubricating oil composition containing the same is introduced into the engine to provide superior soot dispersing ability. The dispersant formulation comprises a first succinimide dispersant and optionally, a second succinimide dispersant, wherein the first and second succinimide dispersants are different. The first dispersant is a succinimide that has been post-treated by a heteroaromatic glycidyl ether shown in Structure I below. The second dispersant is a succinimide with or without post-treatment. In some embodiments, the dispersant formulation includes a third dispersant, wherein the third dispersant is a Mannich dispersant.

In some embodiments, the first and second dispersant may differ in that the first dispersant has been post-treated by the heteroaromatic glycidyl ether while the second dispersant has not been post-treated or post-treated by a secondary post-treating agent. In general, the secondary post-treating agent will be different from the heteroaromatic glycidyl ether (Structure I) used to post-treat the primary succinimide dispersant. Suitable examples of secondary post-treating agent include reactive boron compound, organic carbonate (e.g., ethylene carbonate), organic oxides (e.g., alkylene oxide), glycidol, glycidyl ether, or other post-treatment reagents known in the specialized literature.

Suitable boron compounds that can be used as a source of boron include, for example, boric acid, a boric acid salt, a boric acid ester, and the like. Representative examples of a boric acid include orthoboric acid, metaboric acid, paraboric acid, and the like. Representative examples of a boric acid salt include ammonium borates, such as ammonium metaborate, ammonium tetraborate, ammonium pentaborate, ammonium octaborate, and the like. Representative examples of a boric acid ester include monomethyl borate, dimethyl borate, trimethyl borate, monoethyl borate, diethyl borate, triethyl borate, monopropyl borate, dipropyl borate, tripropyl borate, monobutyl borate, dibutyl borate, tributyl borate, and the like.

Suitable organic carbonates include, for example, cyclic carbonates such as 1,3-dioxolan-2-one (ethylene carbonate); 4-methyl-1,3-dioxolan-2-one(propylene carbonate); 4-ethyl-1,3-dioxolan-2-one(butylene carbonate); 4-hydroxymethyl-1,3-dioxolan-2-one; 4,5-dimethyl-1,3-dioxolan-2-one; 4-ethyl-1,3-dioxolan-2-one; 4,4-dimethyl-1,3-dioxolan-2-one; 4-methyl-5-ethyl-1,3-dioxolan-2-one; 4,5-diethyl-1,3-dioxolan-2-one; 4,4-diethyl-1,3-dioxolan-2-one; 1,3-dioxan-2-one; 4,4-dimethyl-1,3-dioxan-2-one; 5,5-dimethyl-1,3-dioxan-2-one; 5,5-dihydroxymethyl-1,3-dioxan-2-one; 5-methyl-1,3-dioxan-2-one; 4-methyl-1,3-dioxan-2-one; 5-hydroxy-1,3-dioxan-2-one; 5-hydroxymethyl-5-methyl-1,3-dioxan-2-one; 5,5-diethyl-1,3-dioxan-2-one; 5-methyl-5-propyl-1,3-dioxan-2-one; 4,6-dimethyl-1,3-dioxan-2-one; 4,4,6-trimethyl-1,3-dioxan-2-one and spiro[1,3-oxa-2-cyclohexanone-5,5'-1',3'-oxa-2'-cyclohexanone].

Other suitable cyclic carbonates may be prepared from saccharides such as sorbitol, glucose, fructose, galactose and the like and from vicinal diols prepared from C1 to C30 olefins by methods known in the art.

Suitable organic oxides include hydrocarbyl oxides (e.g., alkylene oxides) such as ethylene oxide, propylene oxide, styrene oxide, and the like. A more detailed description of organic oxides is disclosed in U.S. Pat. Nos. 3,373,111 and 3,367,943, which are hereby incorporated by reference.

Glycidols are commercially available reagents of the formula:

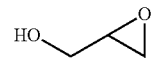

Also, glycidol may be prepared from glycerol-1-monochlorohydrin by the action of potassium hydroxide in alcohol. For example, see Rider et al., JACS, 52, 1521 (1930), which is hereby incorporated by reference.

When formulated together in a lubricating oil, the first and second dispersants work synergistically to impart enhanced dispersancy to the lubricating oil.

In some embodiments, the lubricating oil includes a third dispersant, wherein the third dispersant is a Mannich dispersant.

Primary Dispersant

The primary dispersant of the present invention is a succinimide that has been post-treated by a heteroaromatic glycidyl ether. More specifically, the primary dispersant is a reaction product of (i) a polyalkenyl succinimide and (ii) a heteroaromatic glycidyl ether having the following structure:

Structure I

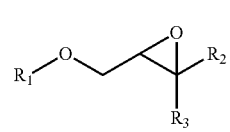

wherein $R_1$ is a heteroaryl or heteroarylalkyl group having about 4 to about 20 carbon atoms. $R_2$ and $R_3$ are independently a hydrogen atom, alkyl group, or aryl group. In some embodiments, at least one of $R_2$ and $R_3$ is a hydrogen atom.

Heteroaryl or heteroarylalkyl groups can be provided by heteroaryl or heteroarylalkyl compounds. Heteroaryl or heteroarylalkyl compounds are generally polycyclic compounds incorporating one or more heterocyclic rings. Specific examples of heteroaryl or hetarylalkyl compounds include, but are not limited to, carbazole, indole, quinoline, indolizine, xanthene, purine, chromene, phenothiazine, benzimidazole, benzotriazole, benzothiazole, dibenzofuran, or a derivative thereof.

The reaction between the succinimide and the heteroaromatic glycidyl ether may proceed under various conditions. A detailed discussion of the reaction is disclosed in U.S. Pat. No. 4,617,137, which is hereby incorporated by reference.

In general, the reaction between succinimide and heteroaromatic glycidyl ether is conducted at a temperature sufficient to cause reaction of the heteroaromatic glycidyl ether with the succinimide. According to one method, reaction temperatures can range from about 0° C. to about 250° C. In some embodiments, reaction temperatures can range from about 50° C. to about 200° C. In some embodiments, reaction temperatures can range from about 100° C. to about 200° C.

The reaction between succinimide and heteroaromatic glycidyl ether may proceed in the presence of a catalyst such as an acidic, basic, or Lewis acid catalyst. Specific examples of catalysts include, for example, boron trifluoride, alkane sulfonic acid, alkali or alkaline carbonate.

Alternatively, the reaction between succinimide and heteroaromatic glycidyl ether may be conducted in a diluent, wherein the reactants are combined in a solvent such as toluene, xylene, base oil and the like. Once the reaction is complete, volatile components may be stripped off.

In some embodiments, the primary succinimide dispersant may be further post-treated by an optional post-treating agent to add additional functionality. Examples of an optional post-treating agent include organic oxide, reactive boron compounds, organic carbonate, and the like.

Hydrocarbyl Succinimide

The hydrocarbyl succinimide can be prepared by any known method such as those described in, for example, U.S. Patent Publication No. 20180034635 and U.S. Pat. No. 7,091,306, which are hereby incorporated by reference.

Hydrocarbyl succinimide can be obtained as the product of a reaction of alkyl-substituted succinic anhydrides with a polyamine. In lubricating oil applications, the succinic anhydrides are typically substituted in alpha position by an alkyl chain such as polyisobutylene (PIBSA) or PIBSA-type moiety. However, any alkyl group compatible with the present invention may be contemplated.

For lubricating oil application, polyalkylene polyamine is commonly used as the polyamine. However, any polyamine compatible with the present invention may be contemplated.

The polyamine can react with the alkyl-substituted succinic anhydride to produce, according to their molar ratio, mono-succinimides, bis-succinimides, tris-succinimides or mixtures of thereof.

In one embodiment, a hydrocarbyl bis-succinimide can be obtained by reacting a hydrocarbyl-substituted succinic anhydride of structure:

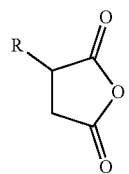

Structure II (wherein R is a hydrocarbyl substituent derived from a polyalkene group having a number average molecular weight of from about 500 to about 3000) with a polyamine.

In one embodiment, R is a hydrocarbyl substituent derived from a polyalkene group having a number average molecular weight of from about 1000 to about 2500. In one embodiment, R is a polyisobutenyl substituent derived from a polyisobutene having a number average molecular weight of from about 500 to about 3000. In another embodiment, R is a polyisobutenyl substituent derived from a polyisobutene having a number average molecular weight of from about 1000 to about 2500.

Suitable polyamines can have a straight- or branched-chain structure and may be cyclic, acyclic, or combinations thereof.

In some embodiments, polyakylene polyamines may be used to prepare the bis-succinimide dispersants. Such polyalkylene polyamines will typically contain about 2 to about 12 nitrogen atoms and about 2 to 24 carbon atoms. Particularly suitable polyalkylene polyamines include those having the formula: $H_2N-(R''NH)_x-H$ wherein R' is a straight- or branched-chain alkylene group having 2 or 3 carbon atoms and x is 1 to 9. Representative examples of suitable polyalkylene polyamines include diethylenetriamine (DETA), triethylenetetramine (TETA), tetraethylenepentamine (TEPA), pentaethylene hexamine (PEHA), and heavier polyalkylene-amines (HPA).

In some embodiments, the polyamine may contain cyclic groups. Specific examples include N, N'-bis-(2-aminoethyl) piperazine) (Bis AEP), N-[(2-aminoethyl) 2-aminoethyl] piperazine) (PEEDA), 1-(2-aminoethyl)-4-[(2-aminoethyl) amino]ethyl]-piperazine) (AEPEEDA) and 1-[2-[[2-[(2-aminoethyl)amino]ethyl]amino]ethyl]-piperazine) (PEDETA).

Many of the polyamines suitable for use in the present invention are commercially available and others may be prepared by methods which are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99 116.

Generally, the hydrocarbyl-substituted succinic anhydride is reacted with the polyamine at a temperature of about 130° C. to 220° C. (e.g., 135° C. to 200° C., 145° C. to 175° C., etc.). The reaction can be carried out under an inert atmosphere, such as nitrogen or argon. Generally, a suitable molar charge of polyamine to polyalkenyl-substituted succinic anhydride is from about 0.35:1 to about 1:1 (e.g., 0.4:1 to 0.75:1). As used herein, the "molar charge of polyamine to polyalkenyl-substituted succinic anhydride" means the ratio of the number of moles of polyamine to the number of succinic groups in the succinic anhydride reactant.

One class of suitable hydrocarbyl succinimides may be represented by the following structure:

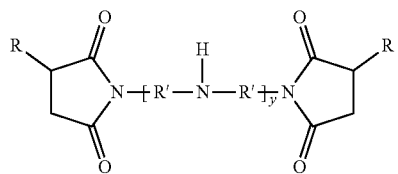

Structure III wherein R and R' are as described herein above and y is 1 to 11.

Heteroaromatic Glycidyl Ether

The heteroaromatic glycidyl ether may be prepared by any known method such as described in, for example, U.S. Pat. No. 7,265,232, which is hereby incorporated by reference.

According to one method, the heteroaromatic glycidyl ether may be obtained by reacting an heteroaryl or heteroarylalkyl alcohol with an epihalohydrin. The reaction may take place in multi-layer solvent system that includes both aqueous and non-aqueous solvents. The reaction may also include aqueous bases such as alkali hydroxide. Furthermore, the reaction may be promoted by the presence of a quaternary ammonium salt. Reaction temperatures may range from about 0° C. to about 50° C.

Secondary Dispersant

The secondary dispersant of the present invention is a succinimide dispersant that is distinct from the primary dispersant of the present invention. According to an embodiment, the secondary succinimide dispersant may be a hydrocarbyl succinimide such as shown in Structure III.

In some embodiments, the secondary dispersant is not post-treated. In other embodiments, the secondary dispersant is post-treated by a secondary post-treating agent. In general, the secondary post-treating agent includes any post-treating compatible with the present invention including one or more agents described above. However, the secondary post-treating agent is different from the heteroaromatic glycidyl ether described in Structure I.

Mannich Dispersant

The lubricating oil composition of the present invention may include a Mannich dispersant. The Mannich dispersant is a dispersant obtained as a product of a Mannich reaction. The Mannich dispersant can be present in about 1.5 wt % to about 20 wt % based on total weight of the lubricating oil composition.

A particularly useful Mannich dispersant is described in U.S. Pat. No. 9,528,074, which is hereby incorporated by reference. This Mannich dispersant can be prepared by the condensation of polyisobutyl-substituted hydroxyaromatic compound, wherein the polyisobutyl group is derived from polyisobutene containing at least about 70 wt % methylvinylidene isomer and has a number average molecular weight in the range of about 400 to about 2500, an aldehyde, an amino acid or ester derivative thereof, and an alkali metal base.

In one embodiment, the Mannich condensation product can be represented by the structure of formula IV:

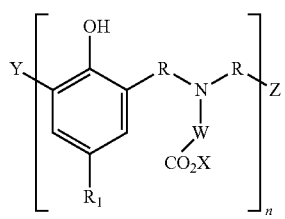

Formula IV wherein each R is independently —CHR'—, R' is a branched or linear alkyl having one carbon atom to about 10 carbon atoms, a cycloalkyl having from about 3 carbon atoms to about 10 carbon atoms, an aryl having from about 6 carbon atoms to about 10 carbon atoms, an alkaryl having from about 7 carbon atoms to about 20 carbon atoms, or aralkyl having from about 7 carbon atoms to about 20 carbon atoms, R1 is a polyisobutyl group derived from polyisobutene containing at least about 70 wt % methylvinylidene isomer and having a number average molecular weight in the range of about 400 to about 2,500; X is hydrogen, an alkali metal ion or alkyl having one to about 6 carbon atoms; W is —[CHR"]-m wherein each R" is independently H, alkyl having one carbon atom to about 15 carbon atoms, or a substituted-alkyl having one carbon atom to about 10 carbon atoms and one or more substituents selected from the group consisting of amino, amido, benzyl, carboxyl, hydroxyl, hydroxyphenyl, imidazolyl, imino, phenyl, sulfide, or thiol; and m is an integer from 1 to 4; Y is hydrogen, alkyl having one carbon atom to about 10 carbon atoms, —CHR'OH, wherein R' is as defined above, or

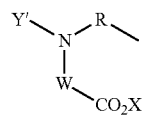

wherein Y' is —CHR'OH, wherein R' is as defined above; and R, X, and W are as defined above; Z is hydroxyl, a hydroxyphenyl group of the formula:

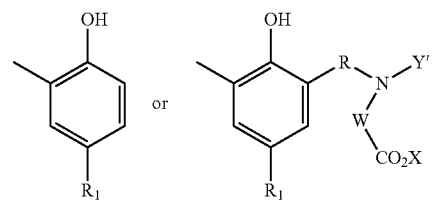

wherein R, R1, Y', X, and W are as defined above, and n is an integer from 0 to 20, with the proviso that when n=0, Z must be:

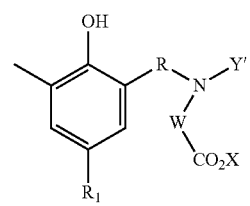

wherein R, R1, Y', X, and W are as defined above.

Lubricating Oil

The lubricating oil composition of the present invention includes a base oil; and a primary succinimide dispersant. In some embodiments, the lubricating oil composition includes a secondary succinimide dispersant. In some embodiments, the lubricating oil composition includes a Mannich dispersant.

The succinimide dispersants of the present disclosure may be useful as dispersant additives in lubricating oils. When employed in this manner, the additives are usually present in the lubricating oil composition in concentrations ranging from 0.001 to 20 wt. % (including, but not limited to, 0.01 to 5 wt. %, 0.2 to 4 wt. %, 0.5 to 3 wt. %, 1 to 2 wt. %, and so forth), based on the total weight of the lubricating oil composition. If other dispersants are present in the lubricating oil composition, a lesser amount of the additive may be used.

Oils used as the base oil will be selected or blended depending on the desired end use and the additives in the finished oil to give the desired grade of engine oil, e.g. a lubricating oil composition having an Society of Automotive Engineers (SAE) Viscosity Grade of 0W, 0W-8, 0W-16, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30, or 15W-40.

The oil of lubricating viscosity (sometimes referred to as "base stock" or "base oil") is the primary liquid constituent of a lubricant, into which additives and possibly other oils are blended, for example to produce a final lubricant (or lubricant composition). A base oil, which is useful for making concentrates as well as for making lubricating oil compositions therefrom, may be selected from natural (vegetable, animal or mineral) and synthetic lubricating oils and mixtures thereof.

Definitions for the base stocks and base oils in this disclosure are the same as those found in American Petroleum Institute (API) Publication 1509 Annex E ("API Base Oil Interchangeability Guidelines for Passenger Car Motor Oils and Diesel Engine Oils," December 2016). Group I base stocks contain less than 90% saturates and/or greater than 0.03% sulfur and have a viscosity index greater than or equal to 80 and less than 120 using the test methods specified in Table E-1. Group II base stocks contain greater than or equal to 90% saturates and less than or equal to 0.03% sulfur and have a viscosity index greater than or equal to 80 and less than 120 using the test methods specified in Table E-1. Group III base stocks contain greater than or equal to 90% saturates and less than or equal to 0.03% sulfur and have a viscosity index greater than or equal to 120 using the test methods specified in Table E-1. Group IV base stocks are polyalphaolefins (PAO). Group V base stocks include all other base stocks not included in Group I, II, Ill, or IV.

Natural oils include animal oils, vegetable oils (e.g., castor oil and lard oil), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful. Natural oils vary also as to the method used for their production and purification, for example, their distillation range and whether they are straight run or cracked, hydrorefined, or solvent extracted.

Synthetic oils include hydrocarbon oil. Hydrocarbon oils include oils such as polymerized and interpolymerized olefins (e.g., polybutylenes, polypropylenes, propylene isobutylene copolymers, ethylene-olefin copolymers, and ethylene-alphaolefin copolymers). Polyalphaolefin (PAO) oil base stocks are commonly used synthetic hydrocarbon oil. By way of example, PAOs derived from $C_8$ to $C_{14}$ olefins, e.g., $C_8$, $C_{10}$, $C_{12}$, $C_{14}$ olefins or mixtures thereof, may be utilized.

Other useful fluids for use as base oils include non-conventional or unconventional base stocks that have been processed, preferably catalytically, or synthesized to provide high performance characteristics.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

Base oils for use in the lubricating oil compositions of present disclosure are any of the variety of oils corresponding to API Group I, Group II, Group III, Group IV, and Group V oils, and mixtures thereof, preferably API Group II, Group III, Group IV, and Group V oils, and mixtures thereof, more preferably the Group III to Group V base oils due to their exceptional volatility, stability, viscometric and cleanliness features.

Typically, the base oil will have a kinematic viscosity at 100° C. (ASTM D445) in a range of 2.5 to 20 mm$^2$/s (e.g., 3 to 12 mm$^2$/s, 4 to 10 mm$^2$/s, or 4.5 to 8 mm$^2$/s).

The present lubricating oil compositions may also contain conventional lubricant additives for imparting auxiliary functions to give a finished lubricating oil composition in which these additives are dispersed or dissolved. For example, the lubricating oil compositions can be blended with antioxidants, ashless dispersants, anti-wear agents, detergents such as metal detergents, rust inhibitors, dehazing agents, demulsifying agents, friction modifiers, metal deactivating agents, pour point depressants, viscosity modifiers, antifoaming agents, co-solvents, package compatibilizers, corrosion-inhibitors, dyes, extreme pressure agents and the like and mixtures thereof. A variety of the additives are known and commercially available. These additives, or their analogous compounds, can be employed for the preparation of the lubricating oil compositions of the invention by the usual blending procedures.

Each of the foregoing additives, when used, is used at a functionally effective amount to impart the desired properties to the lubricant. Thus, for example, if an additive is an ashless dispersant, a functionally effective amount of this ashless dispersant would be an amount sufficient to impart the desired dispersancy characteristics to the lubricant. Generally, the concentration of each of these additives, when used, may range, unless otherwise specified, from about 0.001 to about 20 wt. %, such as about 0.01 to about 10 wt. %.

EXAMPLES

The following examples are intended for illustrative purposes only and do not limit in any way the scope of the present disclosure.

Lubricating Oil Baseline Formulation A

A first baseline lubricating oil composition was prepared by blending together the following components to obtain an SAE 10W-30 viscosity grade formulation:
  (a) mixture of primary and secondary zinc dialkyldithiophosphate;
  (b) bis-succinimide dispersant;
  (c) magnesium sulfonate detergent;
  (d) calcium phenate and calcium sulfonates;
  (e) alkylated diphenylamine and hindered phenol antioxidant;
  (f) molybdenum succinimide antioxidant;
  (g) pour point depressant, viscosity index improver, and foam inhibitor; and
  (h) mixture of Group II base oils.

Comparative Example 1

Comparative example 1 was formulated by adding 2.875 wt % of a non-post-treated succinimide dispersant to baseline formulation A.

Comparative Example 2

Comparative Example 2 was formulated by adding 2.875 wt % of a glycidol post-treated succinimide dispersant to baseline formulation A. Preparation of the glycidol post-treated succinimide dispersant is described below.

A 250 mL 3-neck stirred round bottom flask was charged with 122.24 g of bis-succinimide, which is a reaction product of 2300 MW thermal PIBSA and HPA (1.24 wt % nitrogen). The bis-succinimide was then heated to 35° C. via heating mantel under a nitrogen purge. 2.45 g of glycidol (molecular weight=74.08 g/mole, glycidol: HPA CMR=2) was charged into bis-succinimide dropwise using a syringe over a 30-minute period. The temperature of the mixture was maintained at 35° C. for 16.5 hours. Diluent oil content of final product was 33.8 wt %.

Comparative Example 3

Comparative Example 3 was formulated by adding 2.875 wt % of a glycidol post-treated succinimide dispersant to baseline formulation A. Preparation of the glycidol post-treated succinimide is described below.

A 250 mL 3-neck stirred round bottom flask was charged with 122 g of bis-succinimide, which is a reaction product of 2300 MW thermal PIBSA and HPA (1.24 wt % nitrogen). The bis-succinimide then heated to 35° C. via heating mantel under a nitrogen purge. 4.88 g of glycidol (molecular weight=74.08 g/mole, glycidol: HPA CMR=4) was charged into bis-succinimide dropwise using an addition funnel over a 2-hours period. The temperature of the mixture was maintained at 35° C. for 16.5 hours. Diluent oil content of final product was 33.1 wt %.

Comparative example 3 differs from comparative example 2 in the charge mole ratio used.

Example 1

Inventive Example 1 was formulated by adding of 2.875% of the 4-glycidyloxy carbazole post-treated dispersant described above to the baseline formulation A. Preparation of the 4-glycidyloxy carbazole is described below.

A 250 mL 3-neck stirred round bottom flask was charged with 137.78 g of bis-succinimide, which is a reaction product of 2300 MW thermal PIBSA and HPA (1.21 wt % nitrogen). The bis-succinimide then was heated to 135° C. via heating mantel under a nitrogen purge. 8.72 g of 4-glycidyloxy carbazole (molecular weight=239.27 g/mole, 4-glycidyloxy carbazole: HPA=2) was charged into bis-succinimide over a 2-hour period. The temperature of the mixture was maintained at temperature for 30 minutes. The product had the following properties: TBN=19.8 mg KOH/g, Nitrogen=1.50 wt %, diluent oil content=33.8 wt %.

Soot Thickening Bench Test

Inventive example 1 and comparative examples 1-4 were evaluated for their soot dispersancy. Bench test that measures the ability of the formulation to disperse and control viscosity increase resulting from the addition of carbon black, a soot surrogate, was performed. In this test, each fresh oil sample was treated with VULCAN® XC72R carbon black (Cabot Corporation) and homogenized using a Resodyn LabRAM II acoustic mixer for 4 minutes to completely disperse the carbon black. The KV100 of each lubricating oil sample was then measured at 100° C. using a Zeitfuchs Reversed Flow Cross-Arm Viscometer (Cannon Instrument Company) in a PMT TV4000 temperature bath (Tamson Instruments) according to ASTM D445. The viscosity increase relative to the reference oil sample containing no carbon black is reported. Lower viscosity increase indicates improved soot dispersion performance, whereas higher viscosity increase or gelling of the sample indicates poor dispersancy. The results of the soot thickening bench test are summarized in Table 1 below.

TABLE 1

| Sample | Comp. ex. 1 | Comp. ex. 2 | Comp. ex. 3 | Ex. 1 |
| --- | --- | --- | --- | --- |
| Post-treating agent | None | Glycidol | Glycidol (4 eq.) | 4-glycidyloxy carbazole |
| KV100 (CSt) | 12.33 | 12.38 | 12.53 | 12.11 |
| KV100 @ 3% carbon black (CSt) | 34.22 | 29.13 | *Fail | 18.4 |
| Viscosity increase @ 3% carbon black (CSt) | 21.89 | 16.75 | — | 6.29 |
| KV100 @ 4% carbon black (CSt) | 58.67 | 65.17 | *Fail | 43.73 |
| Viscosity increase @ 4% carbon black (CSt) | 46.34 | 52.79 | — | 31.62 |
| KV100 @ 5% carbon black (CSt) | 98.28 | *Fail | *Fail | 91.07 |
| Viscosity increase @ 5% carbon black (CSt) | 85.95 | — | — | 78.96 |

*Indicates sample gelled upon mixing with carbon black

As seen in Table 1, inventive example 1 demonstrated lower viscosity increase relative to the comparative examples, indicating that the aromatic post-treating agent in example 1 lead to superior soot dispersing ability.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby.

Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

The terms "a" and "the" as used herein are understood to encompass the plural as well as the singular.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art. While the foregoing is directed to embodiments of the present disclosure, other and further embodiments of the disclosure may be devised without departing from the basic scope thereof, and the scope thereof is determined by the claims that follow.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

The invention claimed is:

1. A dispersant composition comprising:
    a succinimide dispersant composition comprising a reaction product of a hydrocarbyl succinimide and a heteroaromatic glycidyl ether having a Structure I:

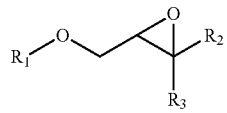

wherein $R_1$ is a heteroaryl or heteroarylalkyl group having 4 to 20 carbon atoms, and $R_2$ and $R_3$ are independently a hydrogen atom, an alkyl group, or an aryl group.

2. The dispersant composition of claim 1, wherein the hydrocarbyl succinimide is a mono-succinimide, bis-succinimide, tris-succinimide or a mixture thereof.

3. The dispersant composition of claim 1, wherein the hydrocarbyl succinimide is the reaction product of at least one succinimide anhydride and a polyamine.

4. The dispersant composition of claim 3, wherein the polyamine is diethylene triamine, a triethylene tetramine, a tetraethylene pentamine, a pentaethylene hexamine, or a poly-alkylene-amine.

5. The dispersant composition of claim 1, wherein the reaction product is further post-treated by an organic oxide, reactive boron compound, or organic carbonate.

6. The dispersant composition of claim 1, further comprising a second succinimide.

7. The dispersant composition of claim 6, wherein the second succinimide has been post-treated by an organic carbonate, glycidol, glycidyl ether different from structure I, organic oxide or reactive boron compound.

8. The dispersant composition of claim 1, wherein at least one of $R_2$ and $R_3$ is a hydrogen atom.

9. The dispersant composition of claim 1, further comprising a dispersant prepared by a Mannich reaction.

10. A lubricating oil composition comprising:
    a base oil;
    a succinimide dispersant composition comprising a reaction product of a hydrocarbyl succinimide and a heteroaromatic glycidyl ether having a Structure I:

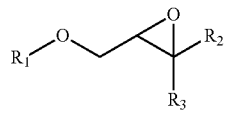

wherein $R_1$ is a heteroaryl or heteroarylalkyl group having 4 to 20 carbon atoms, and $R_2$ and $R_3$ are independently a hydrogen atom, an alkyl group, or an aryl group.

11. The lubricating oil composition of claim 10, wherein the hydrocarbyl succinimide is a mono-succinimide, bis-succinimide, tris-succinimide or a mixture thereof.

12. The lubricating oil composition of claim 10, wherein the hydrocarbyl succinimide is the reaction product of at least one succinimide anhydride and a polyamine.

13. The lubricating oil composition of claim 12, wherein the polyamine is diethylene triamine, a triethylene tetramine, a tetraethylene pentamine, a pentaethylene hexamine, or a poly-alkylene-amine.

14. The lubricating oil composition of claim 10, wherein the reaction product is further post-treated by an organic oxide, reactive boron compound, or organic carbonate.

15. The lubricating oil composition of claim 10, further comprising a second succinimide.

16. The lubricating oil composition of claim 15, wherein the second succinimide has been post-treated by an organic carbonate, glycidol, glycidyl ether different from structure I, organic oxide or reactive boron compound.

17. The lubricating oil composition of claim 10, wherein at least one of $R_2$ and $R_3$ is a hydrogen atom.

18. The lubricating oil composition of claim 10, further comprising a dispersant prepared by a Mannich reaction.

19. A method of reducing soot-induced viscosity increase in an engine, the method comprising:
    introducing a dispersant composition to the engine, wherein the dispersant composition comprises:
        a succinimide dispersant comprising a reaction product of a polyalkenyl succinimide and a heteroaromatic glycidyl ether having a Structure I:

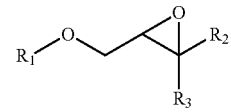

wherein $R_1$ is a heteroaryl or heteroarylalkyl group having 4 to 20 carbon atoms, and $R_2$ and $R_3$ are independently a hydrogen atom, an alkyl group, or an aryl group; and
    operating the engine.

20. The method of claim 19, wherein the hydrocarbyl succinimide is a mono-succinimide, bis-succinimide, tris-succinimide or a mixture thereof.

21. The method of claim 19, wherein the hydrocarbyl succinimide is the reaction product of at least one succinimide anhydride and a polyamine.

22. The method of claim 21, wherein the polyamine is a diethylene triamine, a triethylene tetramine, a tetraethylene pentaamine, a pentaethylene hexamine, or a poly-alkylene-amine.

23. The method of claim 19, wherein the dispersant composition further comprises a second succinimide.

24. The method of claim 23, wherein the second succinimide is post treated by an organic oxide, reactive boron compound, or organic carbonate.

25. The method of claim 19, wherein at least one of $R_2$ and $R_3$ is a hydrogen atom.

26. The method of claim 19, further comprising a dispersant made by a Mannich reaction.

* * * * *